US009644114B2

(12) United States Patent
Webb et al.

(10) Patent No.: US 9,644,114 B2
(45) Date of Patent: May 9, 2017

(54) SILANE ENDCAPPED POLYAMIDE RESINS

(71) Applicant: The United States of America, as represented by the Secretary of the Navy, Washington, DC (US)

(72) Inventors: Arthur A. Webb, Bethesda, MD (US); Jozef Verborgt, Dunedin, FL (US)

(73) Assignee: The United States of America, as represented by the Secretary of the Navy, Washington, DC (US)

( * ) Notice: Subject to any disclaimer, the term of this patent is extended or adjusted under 35 U.S.C. 154(b) by 0 days.

(21) Appl. No.: 15/133,604

(22) Filed: Apr. 20, 2016

(65) Prior Publication Data

US 2016/0304746 A1 Oct. 20, 2016

Related U.S. Application Data

(60) Provisional application No. 62/149,930, filed on Apr. 20, 2015.

(51) Int. Cl.
| | |
|---|---|
| *C08G 77/54* | (2006.01) |
| *C09D 183/10* | (2006.01) |
| *C09D 183/08* | (2006.01) |
| *C08G 77/455* | (2006.01) |

(52) U.S. Cl.
CPC .......... *C09D 183/08* (2013.01); *C08G 77/54* (2013.01); *C09D 183/10* (2013.01); *C08G 77/455* (2013.01)

(58) Field of Classification Search
None
See application file for complete search history.

(56) References Cited

U.S. PATENT DOCUMENTS

| | | | |
|---|---|---|---|
| 4,394,517 A * | 7/1983 | Martin | C07F 7/182 252/8.61 |
| 5,223,495 A | 6/1993 | Inoue et al. | |
| 5,554,709 A | 9/1996 | Emmerling et al. | |
| 5,659,001 A * | 8/1997 | de la Croi Habimana | C08L 101/10 528/17 |
| 6,592,659 B1 | 7/2003 | Terrazas et al. | |
| 2009/0232994 A1 | 9/2009 | Ambrose et al. | |

FOREIGN PATENT DOCUMENTS

| | | |
|---|---|---|
| CN | 103087086 A | 5/2013 |
| EP | 0507727 A2 | 10/1992 |
| JP | 2004-317539 A | 11/2004 |

OTHER PUBLICATIONS

"Structure and Photoluminescent Features of Di-amide Cross-linked Alkylene-siloxane Hybrids" authored by Nunes et al. and published in the Journal of Materials Chemistry (2005) 15, 3876-3886.*
Abstract for CN 102786692 (2012).*
"Transparent Polysilsequioxane Films Obtained from Bridged Ureasil Precursors: Tunable Photoluminescence Emission in the Visible Region and Filtering of UV-Radiation" authored by Gomez et al. and published in Macromolecular Materials and Engineering (2010) 295, 1042-1048.*
"Di-amidosils with Tunable Structure, Morphology, and Emission Quantum Yield: the Role of Hydrogen Bonding" authored by Nunes et al. and published in the Journal of Materials Chemistry C (2015) 3, 6844-6861.*
Klapshina et al., "Novel PEG-organized biocompatible fluorescent nanoparticles doped with an ytterbium cyanoporphyrazine complex for biophotonic applications" Chem. Commun., 2010, 46, 8398-8400.
Ladilina et al., "Novel organosilicon monomer for preparing transparent matrices doped with lanthanide complexes" Russian Chemical Bulletin, International Edition, vol. 59, No. 3, pp. 590-597, Mar. 2010.
Peng et al., "Polydiacetylene/Silica Nanocomposites with Tunable Mesostructure and Thermochromatism from Diacetylenic Assembling Molecules" J. Am. Chem. Soc. 2005, 127, 12782-12783.
Tolbert et al., "New Hybrid Organic/Inorganic Polysilsesquioxane?Silica Particles as Sunscreens" ACS Appl. Mater. Interfaces 2016, 8, 3160-3174.
Search Report and Written Opinion in PCT/US2016/028369 (Aug. 9, 2016).

* cited by examiner

*Primary Examiner* — Marc Zimmer
(74) *Attorney, Agent, or Firm* — US Naval Research Laboratory; Joseph T. Grunkemeyer

(57) ABSTRACT

Disclosed herein are compounds having the formula: $R^1$—(CO—NH—$R^2$—$R^3$)$_n$ and polymers made by moisture curing the compound. $R^1$ is an organic group, a dimeric fatty acid chain, a dimeric linoleic fatty acid chain, a trimeric fatty acid chain, a saturated form of any thereof, a residue of a phenalkamine compound, or a residue of a polyamine. Each $R^2$ is an aliphatic group or an aminoaliphatic group. Each $R^3$ comprises an alkoxysilane group. The value n is a positive integer. The compound may be made by reacting a polyester with an amine having an alkoxysilane group or reacting a polyacid with an isocyanate having an alkoxysilane group. Also disclose are compounds made by reacting an amido amine with an epoxy compound.

9 Claims, 4 Drawing Sheets

US 9,644,114 B2

SILANE ENDCAPPED POLYAMIDE RESINS

This application claims the benefit of U.S. Provisional Application No. 62/149,930, filed on Apr. 20, 2015. The provisional application and all other publications and patent documents referred to throughout this nonprovisional application are incorporated herein by reference.

TECHNICAL FIELD

The present disclosure is generally related to polyamide resins having silane groups.

DESCRIPTION OF RELATED ART

Alkoxy terminated polyurea resins have been synthesized and formulated into primers and topcoats. These systems are characterized by the reaction of primary amino silanes with an acrylate to generate a secondary amine via Michael addition. These adducts are further reacted with polyisocyanates to generate a silane functional polyurea resin wherein the secondary amine reacts with the isocyanate to generate the urea component. However, isocyanates have the disadvantage of toxicity.

BRIEF SUMMARY

Disclosed herein is a polymer made by a method comprising: coating a surface with a compound having the formula: $R^1$—$(CO$—$NH$—$R^2$—$R^3)_n$; and moisture curing alkoxysilane groups in the compound to form the polymer. $R^1$ is an organic group. Each $R^2$ is an aliphatic group or an aminoaliphatic group. Each $R^3$ comprises an alkoxysilane group. The value n is a positive integer.

Also disclosed herein is compound having the formula: $R^1$—$(CO$—$NH$—$R^2$—$R^3)_n$. $R^1$ is a dimeric fatty acid chain, a dimeric linoleic fatty acid chain, a trimeric fatty acid chain, a saturated form of any thereof, a residue of a phenalkamine compound, or a residue of a polyamine. $R^2$, $R^3$, and n are as defined above.

Also disclosed herein is a compound made by a method comprising: providing an amine compound having the formula: $R^1$—$(CO$—$NH$—$R^2$—$NH_2)_n$; and reacting the amine compound with an epoxy compound comprising an alkoxysilane group. $R^1$ is an organic group. $R^2$ and n are as defined above.

Also disclosed herein is a method comprising: reacting a polyester compound having the formula $R^1$—$(COOR^5)_n$ with an amine compound having the formula $NH$—$R^2$—$R^3$ to form a compound having the formula $R^1$—$(CO$—$NH$—$R^2$—$R^3)_n$; and moisture curing alkoxysilane groups from the amine compound to form a polymer. Each $R^5$ is an aliphatic group. $R^1$, $R^2$, $R^3$, and n are as defined above.

Also disclosed herein is a method comprising: reacting a polyacid compound having the formula $R^1$—$(COOH)_n$ with an isocyanate compound having the formula $OCN$—$R^2$—$R^3$ to form a compound having the formula $R^1$—$(CO$—$NH$—$R^2$—$R^3)_n$. $R^1$, $R^2$, $R^3$, and n are as defined above.

Also disclosed herein is a method comprising: providing an amine compound having the formula: $R^1$—$(CO$—$NH$—$R^2$—$NH_2)_n$; and reacting the amine compound with an epoxy compound comprising an alkoxysilane group. $R^1$, $R^2$, and n are as defined above.

BRIEF DESCRIPTION OF THE DRAWINGS

A more complete appreciation will be readily obtained by reference to the following Description of the Example Embodiments and the accompanying drawings.

DETAILED DESCRIPTION OF EXAMPLE EMBODIMENTS

In the following description, for purposes of explanation and not limitation, specific details are set forth in order to provide a thorough understanding of the present disclosure. However, it will be apparent to one skilled in the art that the present subject matter may be practiced in other embodiments that depart from these specific details. In other instances, detailed descriptions of well-known methods and devices are omitted so as to not obscure the present disclosure with unnecessary detail.

A series of alkoxysilane terminated polyamide resins have been synthesized and have been formulated into single component (1K) primers and topcoats. The same products can also be formulated into two component (2K) coatings. In particular the use of trans-aminolysis of ester groups with amino silanes is shown to obtain silane end capped polyamides and fatty acid polyamides under favorable conditions by using specific catalysts. Furthermore the reaction of epoxy functional silanes with amine functional polyamide and amido amine resins is shown. Both products are useful for formulating chemically resistant corrosion control primers and weatherable topcoats. Polyamides end capped with silanes can have properties like polyurethanes and polyureas. This is due to the hydrogen bonding of the amide bonds.

Figure 1:
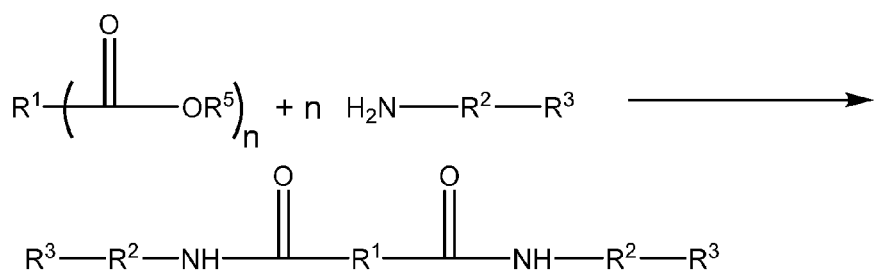
FIG. 1 shows the reaction of an aminosilane with a polyester forming a silane functional polyamide.
Figure 1:
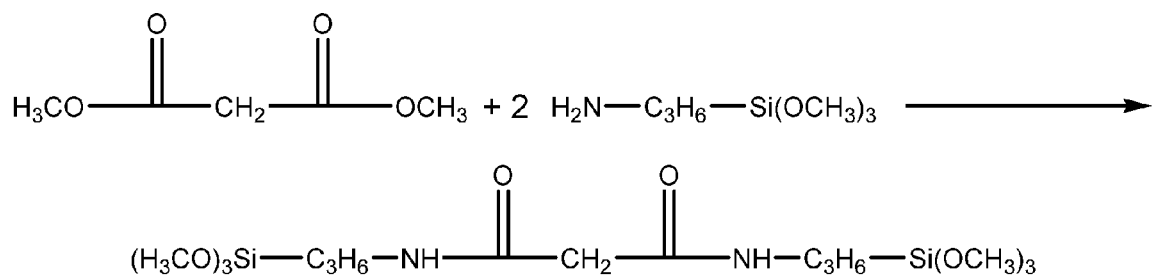

FIG. 1 illustrates the general reaction of an aminosilane with a diester forming a silane functional polyamide. Under this approach a primary amino silane is reacted with either a mono or diester via trans-aminolysis to form a silane terminated polyamide. Such an example is the reaction of amino propyl trimethoxy (or triethoxy) silane with dimethyl malonate (FIG. 1). Using an appropriate catalyst, the reaction proceeds wherein the amino group of the silane reacts with the methyl ester displacing methanol and forming an amide linkage. The methanol remains in solution or can be removed via vacuum distillation. This reaction can be performed using any suitable amino functional silane and ester. The resins produce a very hard fast curing highly chemical resistant film which also possesses excellent adhesion and good thermal stability. It is also possible to add primary and or secondary amines or poly-amines to control the chain length and the percentage of silane in the back bone.

Suitable esters include, but are not limited to, dialkyl malonates, dialkyl adipates, dialkyl azealates, and esters derived from dimeric or trimeric saturated or unsaturated fatty acids. For example, dimeric linoleic acid (commercially available as PRIPOL™ 1009) may include the structures shown below in methyl ester form, as well as other related structures and mixtures of any thereof. Such structures are made by reactions between double bonds, and may also be made from other unsaturated fatty acids, and any mixture of such dimeric or trimeric fatty acids may be used. Saturated fatty acids may have better UV performance than unsaturated fatty acids.

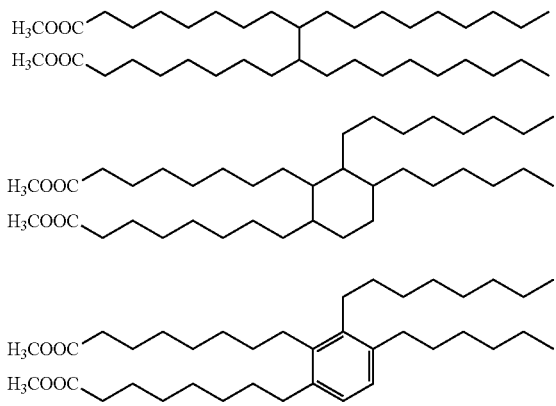

The ester may also be reaction product of any of the above esters with a polyamine. It may be made with 1 mole of the starting ester per reactive amine group. Suitable polyamines include, but are not limited to, a JEFFAMINE® D-series or T-series compound both shown below after reaction with dimethyl malonate and aminopropyl trimethoxysilane.

Figure 2:
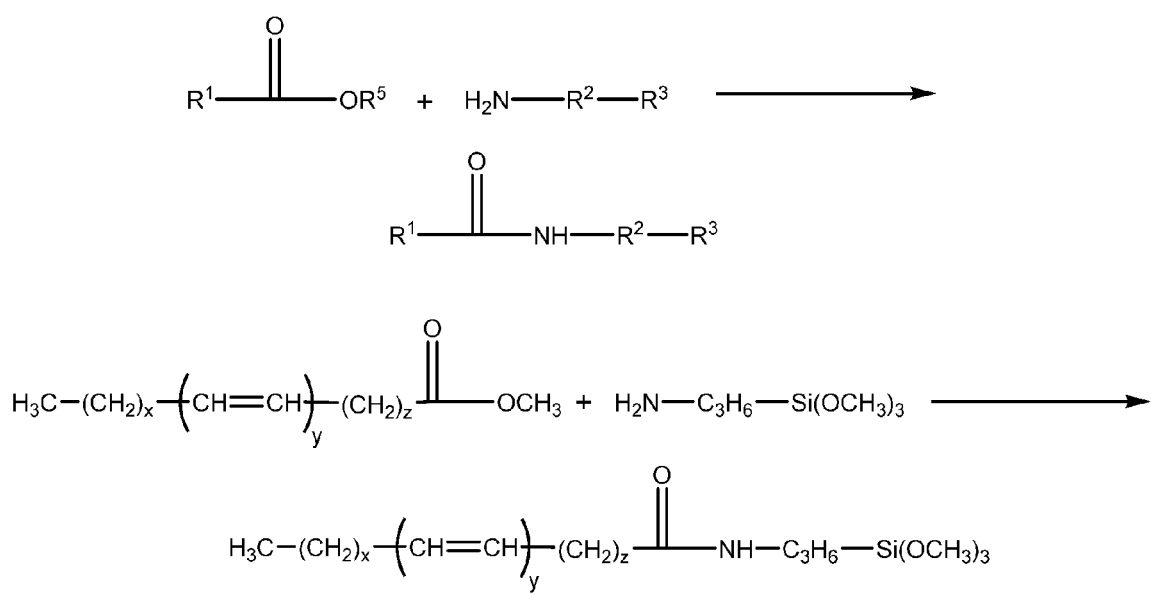
FIG. 2 shows the reaction of an aminosilane with an ester or fatty acid ester forming a silane functional polyamide.

Some embodiments entail the reaction of monomeric, dimeric, and trimeric fatty acid esters with amino propyl trialkoxy silanes under favorable conditions using appropriate catalysts. FIG. 2 illustrates the generation of a silane functional amide fatty acid resin from a monomeric ester. This differs from some of the other examples herein in that the value of n is 1 rather than being greater than 1. Mixtures of mono, dimeric, and trimeric esters can be used. It is also possible to add other diesters, amines, or polyamines to the reaction mix in order to control chain length.

The $R^2$ group bridging the amine to the alkoxysilane group may be an aliphatic group or an aminoaliphatic group, such as n-propylene. The alkoxysilane group contains a silicon atom with at least one alkoxy group bound thereto, such as a trimethoxysilane group.

Figure 3:
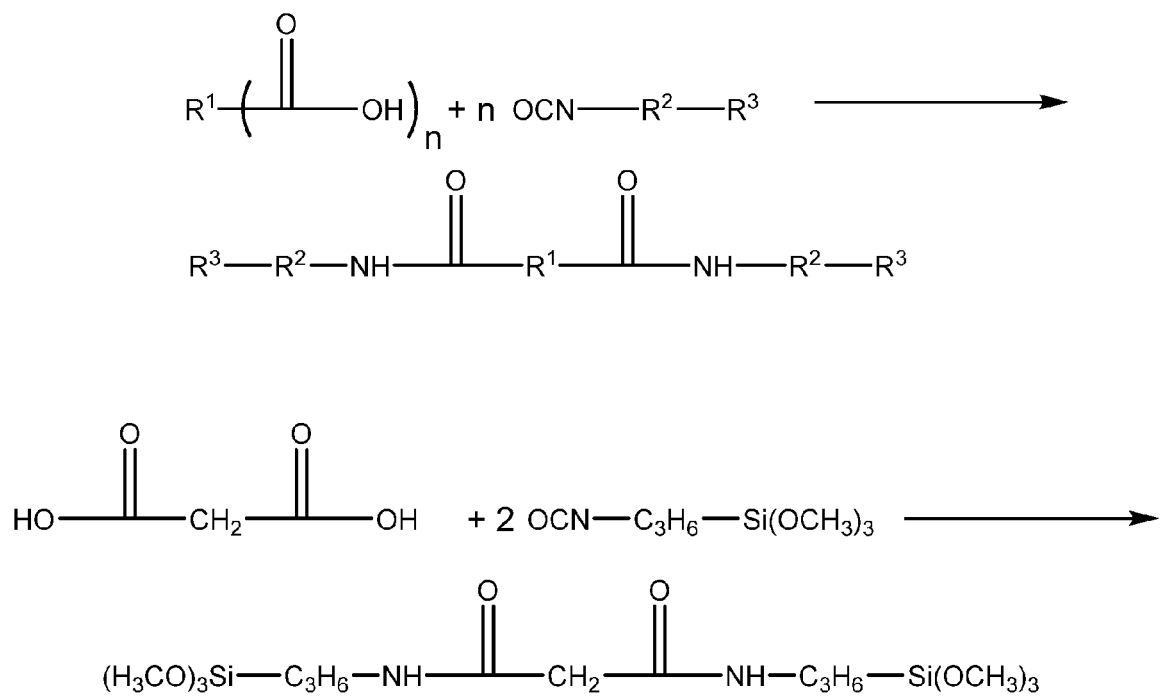
FIG. 3 shows the reaction of an isocyanate with a polyacid forming a silane functional polyamide.

FIG. 3 shows an alternative synthesis using a poly acid instead of a polyester. The poly acid is reacted with an alkoxysilyl monoisocyanate and carbon dioxide is a byproduct.

A polymer may be made from the above silane functional polyamides by coating the compound on a surface and allowing the alkoxysilane groups to crosslink by moisture curing. The moisture curing reaction for methoxysilane groups is shown below. The alcohol product may evaporate from the surface.

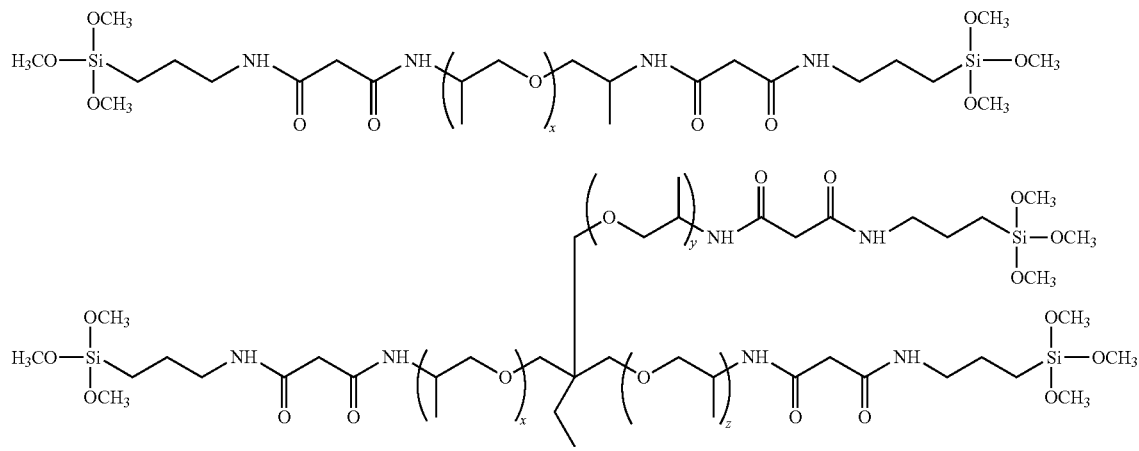

Phenalkamines having aliphatic polyamine substituents attached to a benzene ring may also be used as the polyamine. An example phenalkamine is shown below after reaction with dimethyl malonate. The polyamine moiety of the phenalkamine may be any polyamine, including but not limited to, ethylene diamine, diethylene triamine, or xylylene diamine.

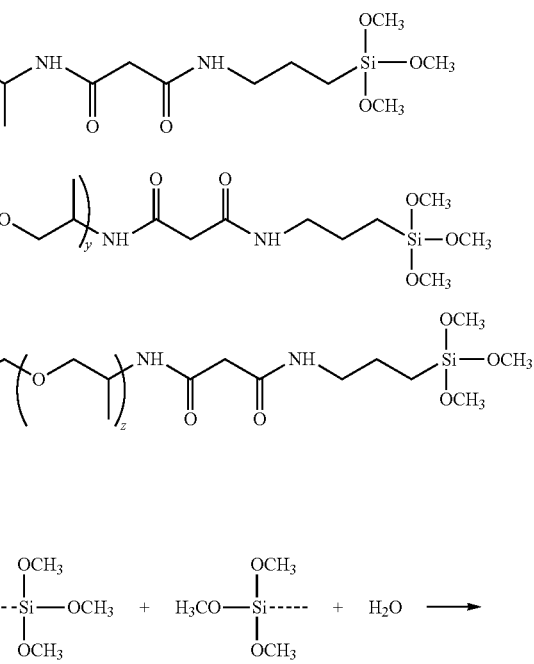

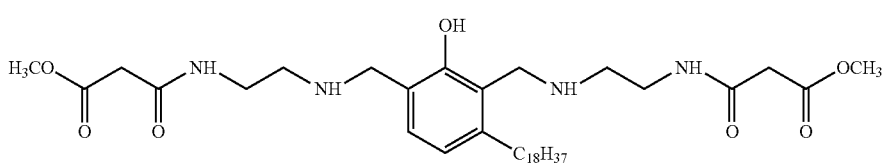

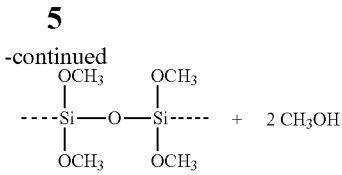 + 2 CH$_3$OH

Figure 4:
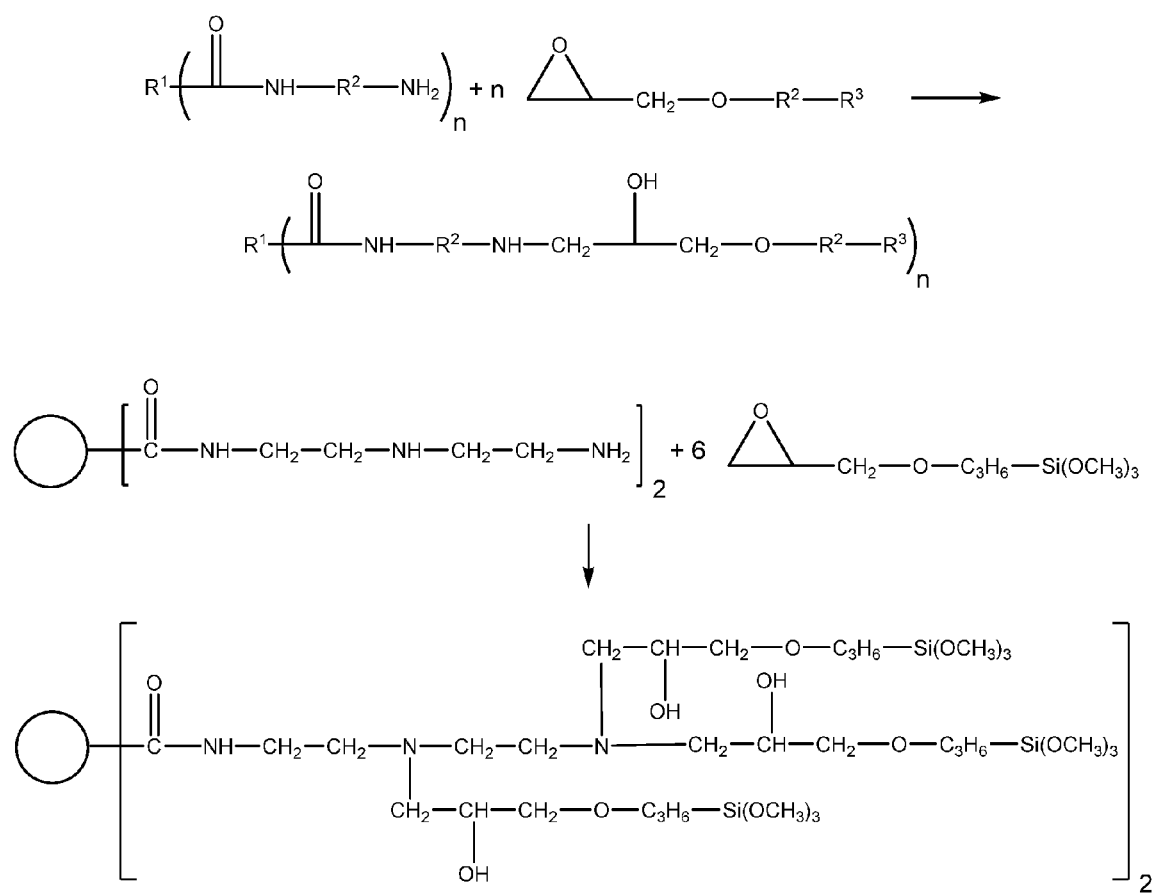
FIG. 4 shows the reaction of an amido amine with an epoxy.

Another embodiment involves the reaction of epoxy functional silanes with amine functional polyamides and amido amine resins as are typically employed for the curing is epoxy resins for structural and coatings applications. FIG. 4 illustrates the general reaction and the reaction of glycidoxypropyl-trimethoxysilane with a typical amine functional polyamide resin derived from the reaction of a dimerized fatty acid with excess low molecular weight amine. The circle represents the bulk of the fatty acid chains. In this approach, the epoxy silane adds directly to the amine in both the primary and secondary state to form silane functionality on the reactive amine. The primary amines are the preferred reaction site as shown in the upper reaction in FIG. 4. In the case of the polyamide and amido amine resins, no reaction occurs between the epoxy silane and the amide groups. The result is a highly crosslinkable resin system that moisture cures by the same reaction as the other silanes above.

The following examples are given to illustrate specific applications. These specific examples are not intended to limit the scope of the disclosure in this application.

Example 1

Dimeric Fatty Acid Methyl Ester Based Resin—

A three necked glass reactor was fitted with a magnetic stirrer, thermometer, and small distilling column with cooler and receiver. A total of 598 grams (1 mol) of dimeric fatty acid methyl ester (PRIPOL™ 1009) was mixed with 358 grams of amino propyl trimethoxy silane (2 mol) and one gram of dibutyl tin dilaurate (DBT) as a catalyst. The mixture was gently heated to 140° C. when methanol was being formed. Heating was continued over a three hour period to remove a total of 64 grams of methanol. The reaction temperature rose to 200-210° C. A mild vacuum was applied to remove any volatile material. The mixture was cooled down to about 60° C. and 100 grams of butyl propionate as solvent was added.

Other possible catalysts that can be used are diazobicycloundecene (DBU) or triazabicyclodecene (TBD) or enzyme based transamination catalysts.

The resulting resin is suitable to be used as a polysiloxane resin with outstanding weathering properties. About 0.25% of DBT was used to promote the moisture curing of the resin.

Example 2

Dimethyl Adipate Based Resin—

A total of 174 grams (1 mol) of dimethyl adipate was mixed with 358 grams of amino propyl trimethoxy silane and one gram of DBT as a catalyst. The mixture was heated gently to 145° C. when methanol started to boil off. A total of 64 grams of methanol was removed when the temperature reached about 210° C. A mild vacuum was applied to remove any volatile material. The neat resin has a low viscosity and can be used without adding any solvent to formulate high heat resistant coatings. The adipate based resin system can be used advantageously as a dipodal silane additive to improve adhesion of coatings to difficult substrates.

Example 3

Dimethyl Malonate Based Resin—

264 grams of dimethyl malonate ester (1 mol) was mixed with 358 grams of amino propyl trimethoxy silane and one gram of DBT as a catalyst. The reaction mixture was gently heated to 110° C. when methanol started to evolve. A total of 64 grams of methanol was removed when the temperature reached 190° C. The neat resin is sufficiently low in viscosity to be used without any solvent and can be used advantageously to formulate high heat and fire resistant coatings. The resin can also be used as a dipodal silane additive to promote adhesion of coatings on difficult substrates.

Example 4

Fatty Acid Methyl Ester Based Resin—

278 grams (based on average C18 fatty acids in soybean and linseed oils) of methyl ester fatty acid (soya, linseed) were mixed with 179 grams of amino propyl trimethoxy silane and 1 gram of TBD catalyst. The reaction mixture was gently heated and methanol started to evolve at around 145° C. The reaction was continued until the theoretical amount of methanol (32 grams) was received. A mild vacuum was applied to remove all volatile material.

The neat resin system has a low viscosity and can be used as such without any solvent. Depending on the amount of conjugated double bonds the resin can be used as a primer with a dual curing system. The silane end groups can be moisture cured by adding organo tin catalyst and the double bonds can be cured oxidatively by adding the standard dries like used in alkyd paints like cobalt, calcium, and many others known to those skilled in the art of alkyd paints. The product can also be used as a reactive diluent in oil based coatings or as a porosity filler for metal sprayed coatings.

Example 5

Fatty Acid Methyl Ester Based Resin—

222 grams of amino ethyl amino propyl trimethoxy silane (1 mol) was mixed with 556 grams of fatty acid methyl ester (soya, linseed) and 1.5 grams of TBD catalyst. The reaction mixture was heated gently and methanol started to evolve at 145° C. The reaction was continued until the theoretical amount of methanol was received at about 220° C.

The resin system has a low viscosity and can be used without adding solvent as a dual cure (moisture and oxidative drying) resin system for primers or pit fillers of metal spray coatings.

Example 6

JEFFAMINE® D230 Based Resin System—

240 grams of JEFFAMINE® D230 (2 mol NH$_2$ equivalent weights) were mixed with 264 grams (2 mol) of dimethyl malonate and 358 grams (2 mol) of amino propyl trimethoxy silane. One gram of DBT was added as a catalyst. The reaction mixture was heated gently and the methanol started to evolve at about 120° C. The reaction was continued until the theoretical amount of methanol (128 grams) was distilled off at 200° C. The reaction mixture was then cooled to 60 C and 100 grams of butyl propionate was added as solvent.

This resin system can be formulated as a top coat with outstanding weather ability or as a primer with outstanding adhering properties. Flexibility of the resin system can be improved by partially end capping with amino silane. Good results were obtained by reducing the theoretical amount of amino silane to 15% and 30%.

Example 7

JEFFAMINE® D400 Based Resin System—

460 grams (2 mol equivalent weights of $NH_2$) of JEFFAMINE® D400 were mixed with 264 grams (2 mol) of dimethyl malonate and 358 grams (2 mol) of amino propyl trimethoxy silane and 1.5 grams of DBT as a catalyst. The reaction mixture is gently heated and methanol started to evolve at about 120° C. The reaction was continued until the theoretical amount of methanol (128 grams) was removed at a temperature of about 200° C. The reaction mixture was cooled down to 60° C. and 120 grams of butyl propionate were added as a solvent.

This resin system can be formulated into top coats with outstanding weather ability or as primers that will tightly adhere to difficult substrates. Flexibility of this resin system can be improved by reducing the amount of silane end capping to 15 to 30%.

Example 8

JEFFAMINE® T403 Based Resin System—

486 grams of JEFFAMINE® T403 (3 $NH_2$ equivalent weights) were mixed with 396 grams (3 mol) of dimethyl malonate and 358 grams (2 mol) of amino propyl trimethoxy silane. 2 grams of DBT were added as a catalyst. The reaction mixture was gently heated and methanol started to evolve at 120° C. The reaction was continued until the theoretical amount of methanol (5×32=160 grams) was received at about 200° C. The reaction mixture was cooled down to 60° C. and 150 grams of butyl propionate was added as a solvent to bring down the viscosity. It can be

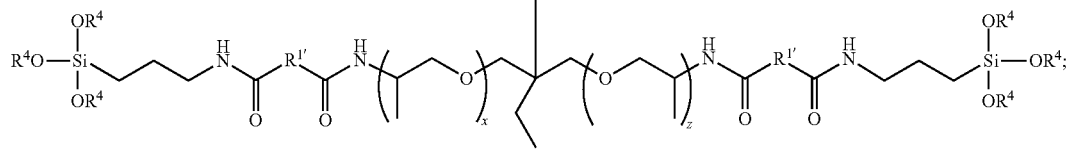

advantageous to add some ethanol as co-solvent to bring down the viscosity even further.

This resin system is only partially end capped with silanes in order to reduce the viscosity and to further improve the flexibility of the resin. The resin can be formulated into top coatings with excellent weather ability.

Obviously, many modifications and variations are possible in light of the above teachings. It is therefore to be understood that the claimed subject matter may be practiced otherwise than as specifically described. Any reference to claim elements in the singular, e.g., using the articles "a", "an", "the", or "said" is not construed as limiting the element to the singular.

What is claimed is:

1. A polymer made by a method comprising:
coating a surface with a compound having the formula:

wherein $R^1$ is a dimeric fatty acid chain, a dimeric linoleic fatty acid chain, a trimeric fatty acid chain, or a saturated form of any thereof;
wherein each $R^2$ is an aliphatic group or an aminoaliphatic group;
wherein each $R^3$ comprises an alkoxysilane group; and
wherein n is a positive integer; and
moisture curing the alkoxysilane groups to form the polymer.

2. A compound having the formula:

wherein $R^1$ comprises a dimeric fatty acid chain, a dimeric linoleic fatty acid chain, a trimeric fatty acid chain, a saturated form of any thereof, a residue of a phenalkamine compound;
wherein each $R^2$ is an aliphatic group or an aminoaliphatic group;
wherein each $R^3$ comprises an alkoxysilane group; and
wherein n is a positive integer.

3. A polymer made by a method comprising:
coating a surface with the compound of claim 2; and
moisture curing the —$OR^4$ groups to form the polymer.

4. A compound having the formula:

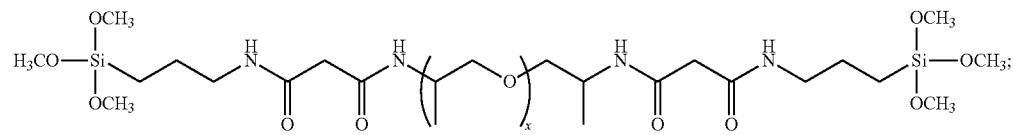

wherein x is a positive integer.

5. A compound having the formula:

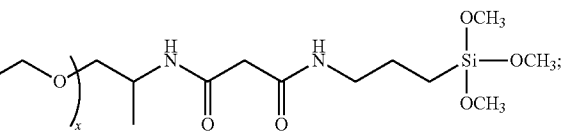
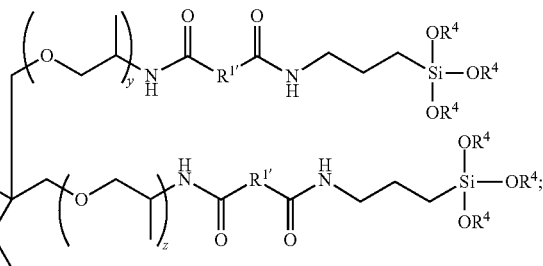

wherein each $R^{1'}$ is an organic group;
wherein each $R^4$ is an alkyl group; and
wherein x, y, and z are each a positive integer.

6. The compound of claim 5, wherein the compound has the formula:

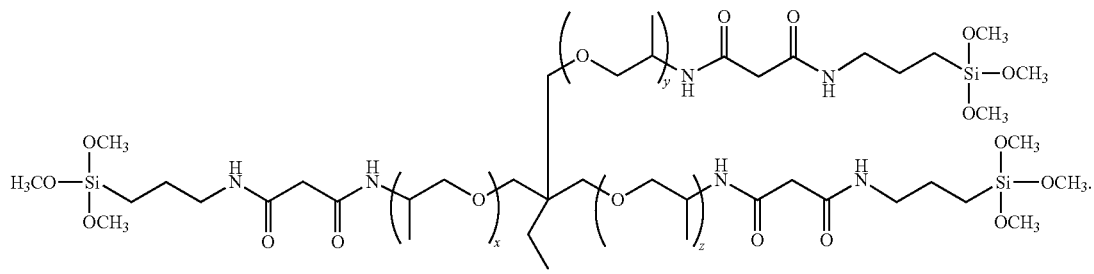

7. A method comprising:
reacting a polyester compound having the formula $R^1$—$(COOR^5)_n$ with an amine compound having the formula $NH_2$—$R^2$—$R^3$ to form a compound having the formula $R^1$—$(CO-NH-R^2-R^3)_n$;
  wherein $R^1$ is a dimeric fatty acid chain, a dimeric linoleic fatty acid chain, a trimeric fatty acid chain, or a saturated form of any thereof;
  wherein $R^2$ is an aliphatic group or an aminoaliphatic group;
  wherein each $R^3$ comprises an alkoxysilane group;
  wherein each $R^5$ is an aliphatic group; and
  wherein n is a positive integer; and
moisture curing the alkoxysilane groups to form a polymer.

8. A method comprising:
reacting a polyacid compound having the formula $R^1$—$(COOH)_n$ with an isocyanate compound having the formula $OCN$—$R^2$—$R^3$ to form a compound having the formula $R^1$—$(CO-NH-R^2-R^3)_n$;
  wherein $R^1$ is a dimeric fatty acid chain, a dimeric linoleic fatty acid chain, a trimeric fatty acid chain, or a saturated form of any thereof;
  wherein each $R^2$ is an aliphatic group or an aminoaliphatic group;
  wherein each $R^3$ comprises an alkoxysilane group; and
  wherein n is a positive integer.

9. The method of claim 8, further comprising:
moisture curing the alkoxysilane groups to form a polymer.

* * * * *